United States Patent [19]

Flashinski

[11] Patent Number: 4,923,897

[45] Date of Patent: May 8, 1990

[54] STABLE AQUEOUS PYRETHROID INSECTICIDAL FORMULATIONS FOR CONTAINMENT IN POLYVINYL CHLORIDE CONTAINERS

[75] Inventor: Stanley J. Flashinski, Racine County, Wis.

[73] Assignee: S. C. Johnson & Son, Inc., Racine, Wis.

[21] Appl. No.: 347,467

[22] Filed: May 4, 1989

Related U.S. Application Data

[63] Continuation of Ser. No. 921,286, Oct. 20, 1986, Pat. No. 4,851,438, which is a continuation of Ser. No. 767,223, Aug. 19, 1985, abandoned.

[51] Int. Cl.$^5$ .............................................. A01N 53/00
[52] U.S. Cl. ...................................... 514/531; 514/970

[58] Field of Search ......................................... 514/531

[56] References Cited

U.S. PATENT DOCUMENTS 3,873,716  3/1975  Fanta ................................... 514/469

*Primary Examiner*—Joseph A. Lipovsky

[57] ABSTRACT

The addition of nonionic surfactants to aqueous pyrethroid insecticidal formulations increases the pyrethroid stability when the formulation is stored in a polyvinylchloride (PVC) container. The pyrethroids can be synthetic or naturally occurring pyrethroids. The nonionic surfactants are alkylphenol ethoxylates, ethoxylated primary alcohols, polyoxyethylene thioethers or mixtures thereof and have HLB values of between about 10 and about 14.

9 Claims, No Drawings

STABLE AQUEOUS PYRETHROID INSECTICIDAL FORMULATIONS FOR CONTAINMENT IN POLYVINYL CHLORIDE CONTAINERS

REFERENCE TO RELATED APPLICATIONS

This patent application is a continuation of my presently pending U.S. Application Ser. No. 921,286 filed Oct. 20, 1986, now U.S. Pat. No. 4,851,438; which, in turn, is a continuation of my earlier U.S. Application Ser. No. 767,223 filed Aug. 19, 1985 (now abandoned), the benefit of which is now claimed for purposes of priority pursuant to 35 USC §120.

BACKGROUND OF THE INVENTION

The present invention relates to a method of increasing the stability of aqueous pyrethroid insecticidal formulations when stored in polyvinyl chloride (PVC) containers. Additionally, the present invention relates to improved pyrethroid insecticidal formulations that are stable in PVC containers.

Synthetic pyrethroid insecticides and naturally occurring pyrethrins, hereinafter collectively referred to as "pyrethroids", are a valuable class of insecticides available for controlling insects. The pyrethroids have very low solubility in water and are generally considered to be water insoluble. Because of their water insolubility, pyrethroids are usually formulated as an oil-in-water emulsion or microemulsion. However, aqueous pyrethroid formulations are unstable in polyvinyl chloride (PVC) containers. PVC containers are generally considered the container of choice because of their cost and ready availability. Due to the instability of aqueous pyrethroid emulsions in PVC containers, aqueous pyrethroid formulations are limited to packaging in glass or other plastic containers.

It is, therefore, desirable to provide a method for increasing the stability of aqueous pyrethroid formulations in PVC containers.

SUMMARY OF THE INVENTION

Briefly, in accordance with the present invention, the stability of aqueous pyrethroid insecticidal formulations is increased, when the aqueous pyrethroid formulations are stored in PVC containers, by the addition to the formulation of an effective stability-enhancing amount of a nonionic surfactant, having an HLB value of between about 10 and about 14. The nonionic surfactant can be an alkylphenol ethoxylate, an ethoxylated primary alcohol, a polyoxyethylene thioether or mixtures of these surfactants.

The present invention also is directed to insecticidal formulations containing (a) a pyrethroid insecticide, (b) water, and (c) an amount of a nonionic surfactant effective to increase the stability of the pyrethroid formulation in a PVC container.

Of particular interest in the practice of the present invention, TRITON-X-100 brand octylphenoxy polyethoxy ethanol surfactant is employed as the surfactant or emulsifing agent for an aqueous pyrethroid insecticidal formulation. The Triton X-100 surfactant is present in amounts of from about 1.0 to about 5.0 percent by weight of the total formulation. The pyrethroid component of the formulation can be any synthetic or naturally occurring pyrethroid. Suitable synthetic pyrethroids include, for example, d-allethrin, esbiothrin, phenothrin, d-phenothrin, resmethrin, allethrin, permethrin, d-trans allethrin, kadethrin, tetramethrin, and mixtures thereof. Additional pesticides can also be included in these formulations.

DETAILED DESCRIPTION OF THE INVENTION

In practicing the present invention, an aqueous pyrethroid insecticidal formulation which is stable in a PVC container is prepared by admixing one or more pyrethroid insecticides with water in the presence of an effective stability enhancing amount of a surfactant selected from the group consisting of an alkylphenol ethoxylate, an ethoxylated primary alcohol, a polyoxyethylene thioether and mixtures thereof. Generally, an effective amount of a nonionic surfactant constitutes at least about 1.0 percent by volume of the total insecticidal formulation. Advantageously, the surfactant is present in an amount of from about 1.0 to about 5.0 percent by weight of the total formulation and preferably from about 1.5 to about 4.0 percent by weight of the total formulation. The pyrethroid insecticides are added to the present stability-enhanced insecticidal formulations in amounts effective to combat specific insecticidal pests for a given application. The optimum concentration for the insecticides is readily determinable to one skilled in the art.

The term "stability", when used herein to describe the action that the surfactants disclosed herein have on the aqueous pyrethroid insecticidal formulations in PVC containers, is meant to encompass the phenomenon that (1) the aqueous pyrethroid formulation substantially maintains its insecticidal activity and weight percent concentration over an extended period of time and (2) the integrity of the emulsion system is maintained. In particular, the increased stability of the pyrethroids in the PVC container is attributable to the nonionic surfactants preventing the migration of the pyrethroid insecticides into the walls of the PVC container.

The nonionic surfactants employed in the practice of the present invention are (a) alkylphenol ethoxylates having a hydrophilic-lipophilic balance (HLB) value of between about 10 and about 14, (b) ethoxylated primary alcohols having an HLB value of between about 10 and about 14, and (c) polyoxyethylene thioethers having an HLB value of between about 10 and about 14. Mixtures of the above surfactants can also be employed in practicing the present invention. These nonionic surfactants are all known compounds and can be prepared employing procedures well known to one skilled in the art. The nonionic surfactants are described in detail in *Kirk-Othmer Encyclopedia of Chemical Technology*, Third Edition, Volume 22, 1983, which is incorporated herein by reference. Additionally, many of the nonionic surfactants disclosed herein are commercially available. See, McCutcheon's, Emulsifiers and Detergents, North American Edition, 1984, which is incorporated herein by reference.

Suitable alkylphenol ethoxylates include octylphenoxy polyethoxy ethanol and nonylphenoxy polyethoxy ethanol each having an HLB value of 10-14. Octylphenoxy polyethoxy ethanols will contain from about 5 to about 12 moles of ethylene oxide and preferably 5, 7, 9 or 10 moles of ethylene oxide. Nonylphenoxy polyethoxy ethanol will contain from about 5 to about 11 moles of ethylene oxide and preferably 5, 6, 9 and 10 moles of ethylene oxide. Commercially available alkylphenol ethoxylates include the following: TRITON X-100, TRITON X-45, TRITON X-114, TRITON N-111, TRITON N-87, TRITON N-101, TRITON N-57, SURFONIC N-60, SURFONIC N-85, SURFONIC N-95, SURFONIC N-100 and SURFONIC N-102.

Suitable ethoxylated primary alcohol surfactants include linear or branched $C_6$-$C_{15}$ primary alcohol ethoxylates having an HLB value of 10-14. The primary alcohol surfactants are sold as mixtures, such as, for example, $C_{12}$-$C_{13}$ linear primary alcohols containing about 6.5 moles of ethylene oxide, $C_{12}$-$C_{15}$ linear primary alcohols containing about 7 or 9 moles of ethylene oxide, $C_{14}$-$C_{15}$ linear primary alcohols containing about 7 moles of ethylene oxide and $C_9$-$C_{11}$ linear primary chemical category containing about 6 moles of ethylene oxide. Commercially available surfactants of this class include NEODOL 25-7, NEODOL 23-6.4, NEODOL 25-9, NEODOL 45-7, NEODOL 91-6, ALFONIC 610-50R and ALFONIC 1012-60.

Suitable polyoxyethylene thioether surfactants include compounds of the formula

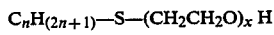

$$C_nH_{(2n+1)}-S-(CH_2CH_2O)_x H$$

wherein n represents 10 to 16, inclusive, and x represents 5 to 12, inclusive. Preferred polyoxyethylene thioethers are those compounds of the above formula wherein n represents 12 and m represents 6 to 10, inclusive. Particularly preferred thioethers are polyethyleneglycol-6 isolauryl thioether, polyethyleneglycol-8 isolauryl thioether and polyethyleneglycol-10 isolauryl thioether. Commercially available polyoxyethylene thioethers include SIPONIC-218, SIPONIC-260, and SIPONIC SK.

Suitable pyrethroid insecticides employed in the present formulations include any synthetic pyrethroid or naturally occurring pyrethrin. Synthetic pyrethroids include allethrin forte, phenathrin, d-phenathrin, tetramethrin, resmethrin, esbiothrin, allethrin, permethrin, d-trans allethrin and kadethrin.

The present aqueous pyrethroid formulations can optionally contain one or more additional ingredients such as additional pesticidal agents, preservatives, dyes, and other known agricultural additives. Such additional pesticidal compounds may be other insecticides, nematocides, arthroprodicides, herbicides, fungicides or bactericides that are compatible with the composition of the present invention. Formalin may be added as a preservative, in concentrations of from about 0.1 to about 0.5 percent by weight of the total formulation.

The present aqueous pyrethroid formulations are prepared employing standard emulsion preparation technology. While the exact order of admixing the ingredients of the present formulation is not critical to the practice of the present invention, it is preferred to disperse the pyrethroid insecticides and any optional ingredients, i.e. preservatives or additional pesticides, into the nonionic surfactant. Warm water is added slowly to this dispersion with agitation to form an emulsion and, preferably, a transparent microemulsion.

In one embodiment of the present invention, the following ingredients are admixed according to the above described procedures to form aqueous pyrethroid insecticidal formulations according to the present invention which are stable in a PVC container:

| INGREDIENTS | WEIGHT PERCENT |
|---|---|
| Pyrethroid insecticide | 0.10-1.00 |
| Triton X-100 brand nonionic insecticide (HLB = 13.5) | 1.00-5.00 |
| Formalin (preservative) | 0-0.50 |
| Water (qs 100) | Balance to 100% |

The above formulation is stable in a PVC container and can be packaged and sold in a ready-to-use spray top PVC bottle. Suitable pyrethroid insecticides for use in the above formulation include d-allethrin, esbiothrin, tetramethrin, allethrin, d-trans allethrin, and kadethrin which are commonly used as knockdown insecticides. Phenothrin, d-phenothrin, resmethrin, permethrin, and cypermethrin can be employed in the above formulation as a kill insecticide. It is preferred to employ a combination of one or more knockdown insecticides plus one or more kill insecticides in the same formulation to provide an effective insecticidal product.

In a preferred embodiment of the present invention the following ingredients are admixed according to the procedures described herein to prepare an insecticidal formulation possessing desirable knockdown and kill characteristics:

| | WEIGHT PERCENT | |
|---|---|---|
| INGREDIENTS | RANGE | PREFERRED |
| PYNAMIN FORTE insecticide* | 0.05-0.50 | 0.30 |
| SUMITHRIN insecticide* | 0.05-0.30 | 0.15 |
| Formalin | 0-0.50 | 0.25 |
| TRITON X-100 nonionic surfactant (HLB = 13.5) | 1.00-5.00 | 2.5 |
| Water (deionized) | Balance to 100% | 96.8 |

*insecticides are expressed as percent active ingredient

The above preferred formulation is stable in PVC containers and is ready for use as a household or industrial insecticide.

The following examples illustrate the practice of the present invention but should not be construed as limiting its scope. Insecticide concentrations are expressed as percent active ingredient.

EXAMPLE 1

Ingredients: Formulation A was prepared employing the following ingredients:

| FORMULATION A | Weight Percent |
|---|---|
| PYNAMIN FORTE insecticide | 0.30 |
| SUMITHRIN insecticide | 0.15 |
| Formalin | 0.25 |
| TRITON X-100 nonionic surfactant (HLB = 13.5) | 2.50 |
| Deionized water | 96.80 |

The pynamin forte, sumithrin and formalin were dispersed in TRITON X-100 surfactant which was warmed to about 100° F. to aid in the rate of dispersion. Warm water (120°F.) was added to a pyrethroid/formalin/TRITON dispersion with agitation to form a transparent microemulsion.

EXAMPLE 2

Employing substantially the same procedures of Example 1, the following transparent microemulsion insecticidal formulations were prepared:

|  | Weight Percent |
|---|---|
| FORMULATION B |  |
| PYNAMIN FORTE insecticide | 0.30 |
| SUMITHRIN insecticide | 0.15 |
| NEODOL 25-7 nonionic surfactant (HLB = 12.2) | 2.50 |
| Water | 97.05 |
| FORMULATION C |  |
| PYNAMIN FORTE insecticide | 0.30 |
| SUMITHRIN insecticide | 0.15 |
| Siponic-218 nonionic surfactant (HLB = 13.9) | 2.50 |
| Water | 97.05 |
| FORMULATION D |  |
| PYNAMIN FORTE insecticide | 0.30 |
| SUMITHRIN insecticide | 0.15 |
| TRITON X-100 nonionic surfactant | 2.50 |
| Water | 97.05 |

EXAMPLE 3

The Formulations 1 and 2, below, were prepared employing substantially the same procedures described in Example 1:

|  | WEIGHT PERCENT |
|---|---|
| FORMULATION 1 |  |
| PYNAMIN FORTE insecticide | 0.30 |
| SUMITHRIN insecticide | 0.15 |
| TRITON X-100 nonionic surfactant (HLB = 13.5) | 2.50 |
| Formalin | 0.25 |
| Deionized water | 96.85 |
| FORMULATION 2 |  |
| PYNAMIN FORTE insecticide | 0.30 |
| SUMITHRIN insecticide | 0.15 |
| TRITON X-193 alkylpolyether and organic sulfonate surfactant | 2.50 |
| Formalin | 0.25 |
| Deionized water | 96.80 |

Samples of Formulation 1 and Formulation 2 were packaged in PVC containers and stored at either 70° F. or 100° F. for 16 months. These samples were analyzed at initial packaging (zero time), 10 months at the designated temperature and 16 months at the designated temperature. The results of the analysis are listed below in Table I in weight percent.

TABLE I

| | FORMULATION | | | |
|---|---|---|---|---|
| | 1 (TRITON X-100) | | 2 (TRITON X-193) | |
| Temp/Time | PYNAMIN FORTE | SUMI-THRIN | PYNAMIN FORTE | SUMI-THRIN |
| At 70° F. | | | | |
| 0 time | 0.29 | 0.18 | 0.29 | 0.17 |
| 10 months | 0.32 | 0.16 | 0.29 | 0.15 |
| 16 months | 0.32 | 0.18 | 0.31 | 0.18 |
| At 100° F. | | | | |
| 0 time | 0.29 | 0.18 | 0.29 | 0.17 |
| 10 months | 0.31 | 0.16 | 0.18 | 0.11 |
| 16 months | 0.30 | 0.18 | 0.16 | 0.11 |

EXAMPLE 4

Employing substantially the same procedures described in Example 1, the following ingredients were admixed to prepare Formulations 3 and 4:

| FORMULATION 3 | Weight Percent |
|---|---|
| Esbiothrin | 0.22 |
| SUMITHRIN insecticide | 0.17 |
| TRITON X-193 alkylpolyether and organic sulfonate surfactant | 2.50 |
| Formalin | 0.25 |
| Deionized water | 96.86 |

| FORMULATION 4 | Weight Percent |
|---|---|
| Esbiothrin | 0.22 |
| SUMITHRIN insecticide | 0.17 |
| TRITON X-100 nonionic surfactant (HLB = 13.5) | 2.50 |
| Formalin | 0.25 |
| Deionized water | 96.86 |

Samples of Formulations 3 and 4 were packaged in PVC containers and stored at 100° F. The samples were analyzed initially and after 10 months. The results of the analysis are listed in Table II below in weight percent.

TABLE II

| | FORMULATION | | | |
|---|---|---|---|---|
| | 3 (TRITON X-193) | | 4 (TRITON X-100) | |
| TIME AT 100° F. | Esbiothrin | SUMITH-RIN | Esbiothrin | SUMITH-RIN |
| 0 time | 0.21 | 0.17 | 0.22 | 0.17 |
| 10 months | 0.14 | 0.13 | 0.22 | 0.17 |

EXAMPLE 5

Employing substantially the same procedures as described in Example 1, the following formulations were prepared for comparative purposes. The formulations contained identical ingredients (Sumithrin, 0.15%; Pynamin Forte, 0.30%; emulsifier, 2.5%; and the balance being water) with the exception that the following emulsifiers were substituted for the nonionic surfactants of the present invention. The formulations and the particular emulsifier employed in each formulation with a description of the emulsifier is given below:

| FORMU-LATION | EMULSIFIER/DESCRIPTION | TYPE |
|---|---|---|
| E | TRITON X405/Octylphenoxy polyethoxy ethanol (HLB = 17.9) | Nonionic |
| F | TWEEN 60/Sorbitan monostearate | Nonionic |
| G | TWEEN 80/Sorbitan monostearate | Nonionic |
| H | NEODOL 5-12/Ethoxylated 1° alcohol (HLB = 14.4) | Nonionic |
| I | MONAMID 150 ADY/Fatty acid alkanolamide | Nonionic |
| J | WITCONAL 14/Polyglycerol fatty acid ester | Nonionic |
| K | TRITON X193/Alkylpolyether and organic sulfonate | Nonionic & Anionic |
| L | SIPONATE 330/Alkyl aryl sulfonate | Anionic |
| M | MONAMINE AC 100/Long chain alkanolamide | Anionic |
| N | MONAWET MO 70E/Dioctyl Na sulfosuccinate | Cationic |
| P | BTC 2125/Quaternary ammonium | Cationic |

| FORMULATION | EMULSIFIER/DESCRIPTION | TYPE |
|---|---|---|
| | chloride | |
| Q | TRITON QS 15/Na salt of amphoteric surfactant | Amphoteric |

The formulations E-Q were compared with formulations B, C and D of Example 2 in an accelerated stability test. The samples of formulations B, C, D and E-Q were packaged in PVC containers and stored at 125° F. for three months. All of the samples were analyzed for pynamin forte and sumithrin content by weight percent at the start of the test and after three months. The results of this accelerated test are listed below in Table III:

TABLE III

| FORMULATION | PYNAMIN FORTE (CONC.) | | SUMITHRIN (CONC.) | |
|---|---|---|---|---|
| | Initial | 3 months | Initial | 3 months |
| B | 0.29 | 0.26 | 0.16 | 0.16 |
| C | 0.30 | 0.23 | 0.17 | 0.13 |
| D | 0.30 | 0.25 | 0.17 | 0.14 |
| E | 0.28 | 0.02 | 0.15 | 0.01 |
| F | 0.29 | 0.07 | 0.16 | 0.12 |
| G | 0.27 | 0.16 | 0.16 | 0.10 |
| H | 0.28 | 0.11 | 0.16 | 0.06 |
| I* | 0.30 | 0.25 | 0.16 | 0.20 |
| J* | 0.29 | 0.32 | 0.16 | 0.19 |
| K | 0.30 | 0.19 | 0.15 | 0.11 |
| L | 0.27 | 0.20 | 0.16 | 0.14 |
| M | 0.29 | 0.09 | 0.17 | 0.12 |
| N | 0.30 | 0.13 | 0.17 | 0.10 |
| O | 0.22 | 0.05 | 0.12 | 0.03 |
| P | 0.28 | 0.06 | 0.17 | 0.04 |
| Q | 0.28 | 0.01 | 0.16 | 0.01 |

*Formulations I and J separated and had a visible residue.

In other representative operations, various pyrethroids and alkylphenol ethoxylates, ethoxylated primary alcohols, and polyoxyethylene thioethers and mixtures thereof are formulated in amounts within the scope of the present invention with water to form aqueous pyrethroid insecticidal formulations which are stable in PVC containers.

I claim:

1. In combination with a polyvinyl chloride container, an aqueous insecticidal composition for containment in the polyvinyl chloride container, the aqueous insecticidal composition comprising water, wherein the improvement comprises:

the aqueous insecticidal composition further comprising:
at least one pyrethroid insecticide in the water; and
an effective amount of a nonionic surfactant selected from the group consisting of an alkylphenol ethoxylate, an ethoxylated primary alcohol, a polyoxyethylene thioether, and mixtures thereof, and having an HLB value of about 10 to about 14, for producing an aqueous pyrethroid insecticidal formulation that is able to maintain its insecticidal activity and integrity when contained in the polyvinyl chloride container;
the thus-produced aqueous pyrethroid insecticidal formulation being contained within the polyvinyl chloride container.

2. The combination in accordance with claim 1, wherein the aqueous pyrethroid insecticidal formulation includes an additional ingredient selected from the group consisting of a pesticidal agent, a preservative, a dye, an agricultural additive, and mixtures thereof.

3. The combination in accordance with claim 2, wherein the pesticidal agent is selected from the group consisting of nematrocide, an arthropodicide, an herbicide, a fungicide, and a bactericide.

4. The combination in accordance with claim 2, wherein the preservative is formalin, and wherein the formalin is present in a concentration of about 0.1 to about 0.5 weight percent based upon the weight of the aqueous pyrethroid insecticidal composition.

5. The combination in accordance with claim 2, wherein the nonionic surfactant is present in an amount of about 1.0 to about 5.0 percent by weight of the aqueous pyrethroid insecticidal composition.

6. The combination in accordance with claim 2, wherein the nonionic surfactant is present in an amount of about 1.5 to about 4.0 percent by weight of the aqueous pyrethroid insecticidal composition.

7. The combination in accordance with claim 2, wherein the nonionic surfactant is octylphenoxy polyethoxy ethanol, the nonionic surfactant being present in an amount of about 1.0 to about 5.0 percent by weight of the aqueous pyrethroid insecticidal composition.

8. The combination in accordance with claim 1, wherein the pyrethroid insecticide is selected from the group consisting of d-allethrin, esbiothrin, phenothrin, d-phenothrin, resmethrin, allethrin, permethrin, d-trans allethrin, kadethrin, tetramethrin, and mixtures thereof.

9. The combination in accordance with claim 1, wherein the aqueous insecticidal composition comprises at least two different types of pyrethroid insecticides, one such pyrethroid insecticide being a knockdown type of pyrethroid insecticide that is selected from the group consisting of d-allethrin, esbiothrin, tetramethrin, allethrin, d-trans allethrin, and kadethrin, the other such pyrethroid insecticide being a contact-kill type of pyrethroid insecticide that is selected from the group consisting of phenothrin, d-phenothrin, resmethrin, permethrin, and cypermethrin.

* * * * *

UNITED STATES PATENT AND TRADEMARK OFFICE
CERTIFICATE OF CORRECTION

PATENT NO. : 4,923,897

DATED : May 8, 1990

INVENTOR(S) : Stanley J. Flashinski

It is certified that error appears in the above-identified patent and that said Letters Patent is hereby corrected as shown below:

At col. 3, line 48, please delete "arthroprodicides" and substitute the word -- arthropodicides -- in place thereof.

In claim 3, namely, at col. 8, line 18, please delete "nematrocide" and substitute the word -- nematocide -- in place thereof.

Signed and Sealed this

Twenty-third Day of April, 1991

Attest:

HARRY F. MANBECK, JR.

*Attesting Officer*      *Commissioner of Patents and Trademarks*